United States Patent
Hazlebeck et al.

(10) Patent No.: US 8,262,776 B2
(45) Date of Patent: Sep. 11, 2012

(54) PHOTOSYNTHETIC CARBON DIOXIDE SEQUESTRATION AND POLLUTION ABATEMENT

(75) Inventors: David A. Hazlebeck, El Cajon, CA (US); Eric H. Dunlop, Paradise (AU)

(73) Assignee: General Atomics, San Diego, CA (US)

( * ) Notice: Subject to any disclaimer, the term of this patent is extended or adjusted under 35 U.S.C. 154(b) by 968 days.

(21) Appl. No.: 11/549,541

(22) Filed: Oct. 13, 2006

(65) Prior Publication Data

US 2008/0086938 A1    Apr. 17, 2008

(51) Int. Cl.
*B01D 53/14* (2006.01)

(52) U.S. Cl. .......... 95/149; 95/232; 95/235; 95/236; 96/234; 435/266; 435/292.1; 435/293.1; 47/1.4; 44/629; 44/605

(58) Field of Classification Search .......... 95/44, 45, 95/149–240, 51; 96/234–242, 243–371; 435/257.1, 289.1–309.4, 266; 47/1.4; 423/210–248
See application file for complete search history.

(56) References Cited

U.S. PATENT DOCUMENTS

| | | | |
|---|---|---|---|
| 2,658,310 A | 11/1953 | Cook | |
| 2,732,661 A | 1/1956 | Spoehr et al. | |
| 2,854,792 A | 10/1958 | Juda | |
| 2,949,700 A | 8/1960 | Kathrein | |
| 3,108,402 A | 10/1963 | Kathrein | |
| 3,195,271 A | 7/1965 | Golueke et al. | |
| 3,218,758 A | 11/1965 | Konikoff | |
| 3,446,488 A | 5/1969 | Mail et al. | |
| 3,468,057 A | 9/1969 | Buisson et al. | |
| 3,521,400 A | 7/1970 | Ort | |
| 3,926,591 A * | 12/1975 | Wildmoser et al. | 95/180 |
| 3,955,318 A | 5/1976 | Hulls | |
| 3,958,364 A | 5/1976 | Schenck et al. | |
| 4,110,183 A * | 8/1978 | Furuta et al. | 204/157.3 |
| 4,236,349 A | 12/1980 | Ramus | |
| 4,341,038 A * | 7/1982 | Bloch et al. | 47/1.4 |
| 4,417,415 A | 11/1983 | Cysewski et al. | |
| 4,689,017 A * | 8/1987 | Lehti | 434/91 |
| 4,869,017 A * | 9/1989 | Bird et al. | 47/1.4 |
| 4,958,460 A | 9/1990 | Nielson et al. | |
| 5,077,025 A | 12/1991 | Glass | |

(Continued)

OTHER PUBLICATIONS

J. J. Elser and D.R. Dobberfuhl, "Use of dried algae as a food source for zooplankton growth and nutrient release experiments", 1999, Journal of Plankton Research, vol. 21, No. 5, pp. 957-970.*

(Continued)

*Primary Examiner* — Duane Smith
*Assistant Examiner* — Thomas McKenzie
(74) *Attorney, Agent, or Firm* — Nydegger & Associates

(57) ABSTRACT

A system and method for producing biofuel from pollutant-fed algae are disclosed. Specifically, the system includes a scrubber with a chamber for receiving a pollutant-contaminated fluid stream. Further, a scrubber solution is received in the chamber for scrubbing the pollutant-contaminated fluid stream. Also, the system includes a bioreactor that is provided with an input port to receive the scrubber solution with pollutants for use as nutrients to support algae cell growth. Further, the system includes an algae separator that removes the algae from the bioreactor and a device for processing the algae into biofuel. In order to recycle the scrubber solution, the algae separator is in fluid communication with the scrubber. With this arrangement, the effluence from the bioreactor may be recycled for use as the scrubber solution.

20 Claims, 1 Drawing Sheet

U.S. PATENT DOCUMENTS

| | | | |
|---|---|---|---|
| 5,116,506 A | 5/1992 | Williamson et al. | |
| 5,192,355 A * | 3/1993 | Eastin | 71/54 |
| 5,279,963 A | 1/1994 | Hobby | |
| 5,330,913 A | 7/1994 | Nakayama | |
| 5,424,467 A * | 6/1995 | Bam et al. | 554/216 |
| 5,942,117 A | 8/1999 | Hunter et al. | |
| 5,951,875 A | 9/1999 | Kanel et al. | |
| 6,000,551 A | 12/1999 | Kanel et al. | |
| 6,395,521 B1 | 5/2002 | Miura | |
| 6,402,065 B1 * | 6/2002 | Higgins | 241/21 |
| 6,524,486 B2 | 2/2003 | Borodyanski et al. | |
| 6,667,171 B2 * | 12/2003 | Bayless et al. | 435/292.1 |
| 6,875,409 B1 | 4/2005 | Zhou et al. | |
| 2004/0229325 A1 * | 11/2004 | Ruecker et al. | 435/134 |
| 2005/0112735 A1 * | 5/2005 | Zappi et al. | 435/134 |
| 2006/0051274 A1 | 3/2006 | Wright et al. | |
| 2006/0272502 A1 | 12/2006 | Van Grinsven et al. | |
| 2007/0048848 A1 * | 3/2007 | Sears | 435/134 |
| 2007/0113467 A1 * | 5/2007 | Abou-Nemeh | 44/388 |
| 2007/0289206 A1 * | 12/2007 | Kertz | 47/1.4 |
| 2008/0044892 A1 * | 2/2008 | Wu | 435/292.1 |
| 2008/0086937 A1 | 4/2008 | Hazlebeck et al. | |
| 2008/0087165 A1 | 4/2008 | Wright et al. | |
| 2008/0299643 A1 | 12/2008 | Howard et al. | |
| 2009/0081743 A1 | 3/2009 | Hazelbeck et al. | |
| 2010/0120104 A1 | 5/2010 | Reed | |

OTHER PUBLICATIONS

NREL/TP-580-24190, A Look Back at the U.S. Department of Energy's Aquatic Species Program; Biodiesel from Algae, Jul. 1998.

* cited by examiner

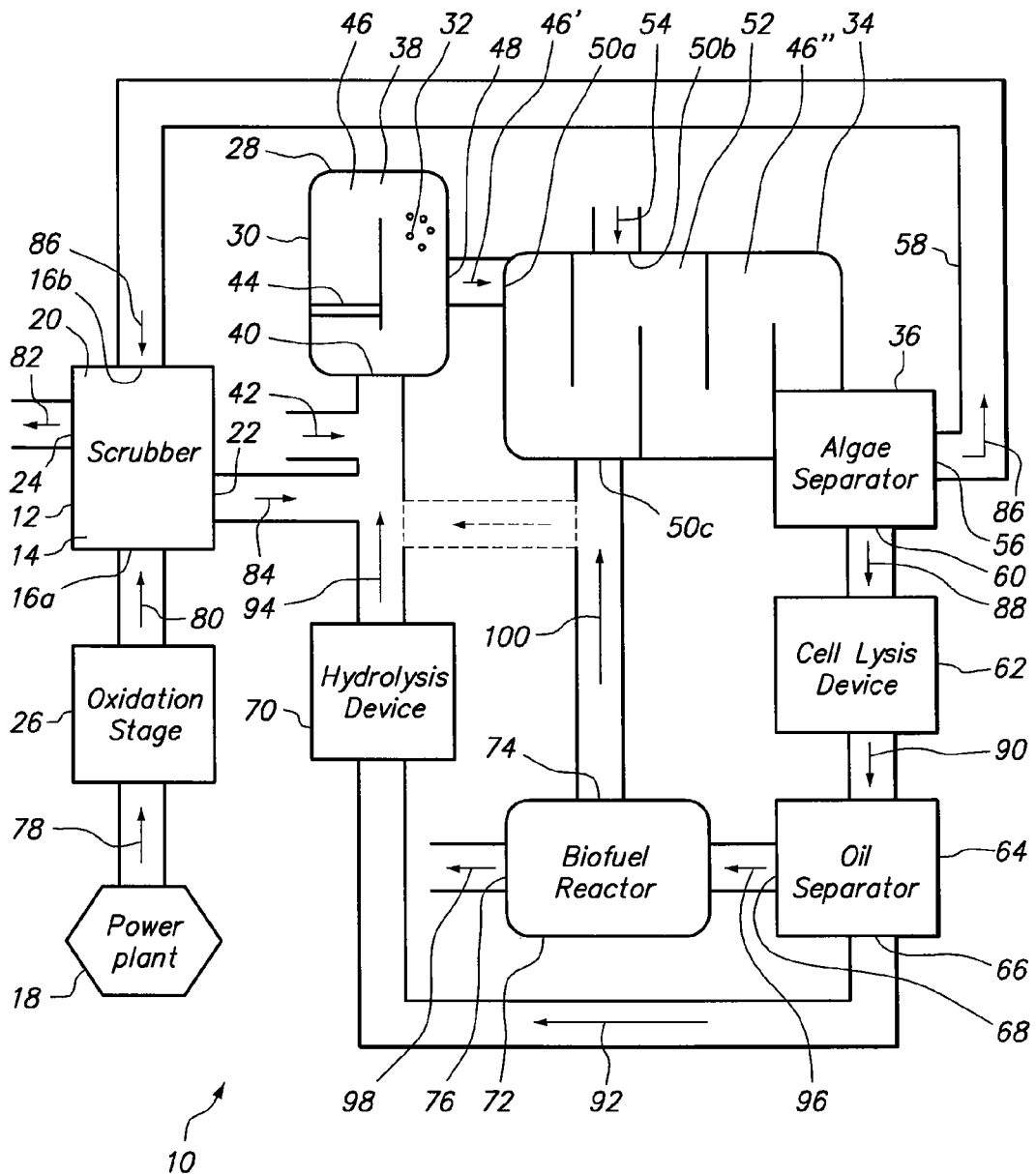

US 8,262,776 B2

PHOTOSYNTHETIC CARBON DIOXIDE SEQUESTRATION AND POLLUTION ABATEMENT

FIELD OF THE INVENTION

The present invention pertains generally to processes for abating pollution and for producing biofuel from algae. More particularly, the present invention pertains to the supply of pollutants to algae cells for use as nutrients to support growth. The present invention is particularly, but not exclusively, useful as a system and method for producing biofuel from algae fed with a scrubber solution that has scrubbed pollutants from a flue gas.

BACKGROUND OF THE INVENTION

As worldwide petroleum deposits decrease, there is rising concern over shortages and the costs that are associated with the production of hydrocarbon products. As a result, alternatives to products that are currently processed from petroleum are being investigated. In this effort, biofuel such as biodiesel has been identified as a possible alternative to petroleum-based transportation fuels. In general, a biodiesel is a fuel comprised of mono-alkyl esters of long chain fatty acids derived from plant oils or animal fats. In industrial practice, biodiesel is created when plant oils or animal fats are reacted with an alcohol, such as methanol.

For plant-derived biofuel, solar energy is first transformed into chemical energy through photosynthesis. The chemical energy is then refined into a usable fuel. Currently, the process involved in creating biofuel from plant oils is expensive relative to the process of extracting and refining petroleum. It is possible, however, that the cost of processing a plant-derived biofuel could be reduced by maximizing the rate of growth of the plant source and by minimizing the costs of feeds needed to support the plant growth. Because algae is known to be one of the most efficient plants for converting solar energy into cell growth, it is of particular interest as a biofuel source. However, current algae processing methods have failed to result in a cost effective algae-derived biofuel.

In overview, the biochemical process of photosynthesis provides algae with the ability to convert solar energy into chemical energy. During cell growth, this chemical energy is used to drive synthetic reactions, such as the formation of sugars or the fixation of nitrogen into amino acids for protein synthesis. Excess chemical energy is stored in the form of fats and oils as triglycerides. Thus, the creation of oil in algae only requires sunlight, carbon dioxide and the nutrients necessary for formation of triglycerides. Nevertheless, with the volume requirements for a fuel source, the costs associated with the inputs are high.

One possible source of carbon dioxide and other nutrients that support cell growth is found in flue gases from power plants or other combustion sources. Further, when present in flue gases, these nutrients are considered pollutants that must be properly disposed of. Therefore, use of nutrients from flue gases to support cell growth will abate pollution.

In light of the above, it is an object of the present invention to provide a system and method for producing algae-derived biofuel which reduces input costs. For this purpose, a number of systems have been developed, such as those disclosed in co-pending U.S. patent application Ser. No. 11/549,532 for an invention entitled "Photosynthetic Oil Production in a Two-Stage Reactor," co-pending U.S. patent application Ser. No. 11/549,552 for an invention entitled "High Photoefficiency Microalgae Bioreactors" and co-pending U.S. patent application Ser. No. 11/549,561 for an invention entitled "Photosynthetic Oil Production with High Carbon Dioxide Utilization," which are filed concurrently herewith and assigned to the same assignee as the present invention, and are hereby incorporated by reference. Another object of the present invention is to provide a system and method for producing algae-derived biofuel that causes pollution abatement. Still another object of the present invention is to provide a system for supplying nutrients to algae cells in the form of pollutants scrubbed from flue gases. Another object of the present invention is to provide a system for recycling the effluent from a medium for growing algae as a scrubber solution. Another object of the present invention is to provide a system for producing algae-derived biofuel that defines a flow path for continuous movement of the algae, its processed derivatives, and the medium fostering its growth. Yet another object of the present invention is to provide a system and method for producing biofuel from pollutant-fed algae that is simple to implement, easy to use, and comparatively cost effective.

SUMMARY OF THE INVENTION

In accordance with the present invention, a system is provided for producing high oil content biofuel from algae fed with pollutants. In this manner, the system serves to produce an environmentally-friendly fuel while abating pollution. Structurally, the system includes a scrubber having a chamber for receiving a pollutant-contaminated fluid stream and a scrubber solution. Typically, the fluid stream comprises flue gas from a combustion source, such as a power plant, which is polluted with carbon dioxide, sulfur oxides, and/or nitrogen oxides. Further, the scrubber solution is typically a caustic or sodium bicarbonate.

For purposes of the present invention, the system also includes a bioreactor for growing algae cells with high oil content. Structurally, the bioreactor includes at least one chemostat and a plug flow reactor. More particularly, the chemostat is a continuously-stirred flow reactor that has an input port, a conduit, and an output port. Preferably, the conduit is formed by an endless, open raceway that receives and holds a medium, and a paddlewheel spanning the conduit is provided to circulate the medium through the conduit. For purposes of the present invention, the plug flow reactor is positioned relative to the chemostat to receive overflow medium containing algae cells from the chemostat. Specifically, the plug flow reactor includes an input port that receives the overflow medium from the output port of the chemostat. Further, the plug flow reactor is in the form of an open raceway that includes a conduit for continuously moving the medium downstream under the influence of gravity.

In addition to the scrubber and bioreactor, the system includes an algae separator. Specifically, the algae separator is positioned in fluid communication with the plug flow reactor to remove the algae cells from the plug flow reactor's conduit. Downstream of the algae separator, the system includes a channel for recycling an effluence from the plug flow reactor to the scrubber for reuse as the scrubber solution. Further, the system includes an apparatus for lysing algae cells to unbind oil from the algae cells. For the present invention, the lysing apparatus is positioned to receive algae cells from the algae separator. Downstream of the lysing apparatus, the system includes an oil separator that receives the lysed cells and withdraws the oil from remaining cell matter. The oil separator has an outlet for the remaining cell matter which is in fluid communication with the chemostat. Further, the system may include a hydrolyzing device that is interconnected between the oil separator and the chemostat. In addition to the cell matter outlet, the oil separator includes an outlet for the oil in fluid communication with a biofuel reactor. In a known process, the biofuel reactor reacts an alcohol with the oil to synthesize biofuel and, as a byproduct, glycerin. Structurally, the biofuel reactor includes a glycerin exit that is in fluid communication with the plug flow reactor.

In operation, the flue gas from the power plant is flowed through the chamber of the scrubber. At the same time, the scrubber solution is sprayed into the scrubber chamber to trap the pollutants in the flue gas. The scrubber solution with the entrapped pollutants is then delivered to the chemostat through its input port. Also, a nutrient mix may be fed into the chemostat through the input port to form, along with the scrubber solution, a medium for growing algae cells. As the paddlewheel circulates the medium through the conduit of the chemostat, the algae cells grow using solar energy and converting the pollutants and other nutrients to cell matter. Preferably, a continuous flow of the medium washes the algae cells and constantly removes them from the chemostat as overflow.

After the overflow medium is removed from the chemostat, it is received in the plug flow reactor and is treated in order to trigger the production of oil in the form of triglycerides in the algae cells. After passing along the conduit of the plug flow reactor, the effluent including algae cells passes through the algae separator which removes the algae cells from the effluent. Thereafter, the effluent is recycled through a channel back to the scrubber for reuse as the scrubber solution. At the same time, the algae cells are delivered to the cell lysis apparatus. Then, the cell lysis apparatus lyses the cells to unbind the oil from the remaining cell matter. This unbound cell material is received by the oil separator from the cell lysis apparatus. Next, the oil separator withdraws the oil from the remaining cell matter and effectively forms two streams of material. The stream of remaining cell matter is transferred to the hydrolysis apparatus where the cell matter is broken into small units which are more easily absorbed by algae cells during cell growth. Thereafter, the hydrolyzed cell matter is delivered to the chemostat to serve as a source of nutrition for the algae cells growing therein. At the same time, the stream of oil is transmitted from the oil separator to the biofuel reactor. In the biofuel reactor, the oil is reacted with an alcohol to form biofuel and a glycerin byproduct. The glycerin byproduct is fed back into the plug flow reactor to serve as a source of carbon for the algae cells therein during the production of intracellular oil.

BRIEF DESCRIPTION OF THE DRAWINGS

The novel features of this invention, as well as the invention itself, both as to its structure and its operation, will be best understood from the accompanying drawing, taken in conjunction with the accompanying description, in which the FIGURE is a schematic view of the system for producing biofuel from pollutant-fed algae in accordance with the present invention.

DESCRIPTION OF THE PREFERRED EMBODIMENTS

Referring to the FIGURE, a system for producing biofuel from pollutant-fed algae in accordance with the present invention is shown and generally designated 10. As shown, the system 10 includes a scrubber 12 for scrubbing a pollutant-contaminated fluid stream. Specifically, the scrubber 12 includes a chamber 14 and an input port 16a for receiving flue gas from a combustion source such as a power plant 18 and a scrubber solution 20. Typically, the flue gas includes pollutants such as carbon dioxide, sulfur oxides, and/or nitrogen oxides. Also, the scrubber solution 20 typically comprises sodium hydroxide or sodium bicarbonate. As further shown, the scrubber 12 includes a solution outlet 22 and a gas outlet 24. Also, the system 10 includes an oxidation stage 26 for oxidizing pollutants in the flue gas to facilitate their removal from the flue gas. As shown, the oxidation stage 26 is interconnected between the power plant 18 and the scrubber 12.

As further shown, the system 10 includes a bioreactor 28 comprised of at least one chemostat 30 for growing algae cells (exemplary cells depicted at 32) and a plug flow reactor 34 for treating the algae cells 32 to trigger cell production of triglycerides. Preferably, and as shown, both the chemostat 30 and the plug flow reactor 34 are open raceways, though closed systems are also contemplated. Further, such open systems 10 can cover several acres of land to optimize economies of scale. For purposes of the present invention, the system 10 includes an algae separator 36 for removing the algae cells 32 from the plug flow reactor 34.

As shown in the FIGURE, the chemostat 30 includes a conduit 38. As further shown, the conduit 38 is provided with an input port 40 that is in fluid communication with the solution outlet 22 of the scrubber chamber 14. For purposes of the present invention, the input port 40 is also in communication with a reservoir (not illustrated) holding a nutrient mix (indicated by arrow 42). Preferably, the nutrient mix 42 includes phosphorous, nitrogen, sulfur and numerous trace elements necessary to support algae growth that are not provided to the bioreactor 28 by the scrubber solution 20. Further, the chemostat 30 is provided with a paddlewheel 44 for causing the medium 46 formed by the scrubber solution 20 and the nutrient mix 42 to continuously circulate around the conduit 38 at a predetermined fluid flow velocity. Also, each conduit 38 is provided with an output port 48 in communication with the plug flow reactor 34.

As shown, the plug flow reactor 34 includes an input port 50a for receiving overflow medium (indicated by arrow 46') with algae cells 32 from the output port 48 of the chemostat 30. As further shown, the plug flow reactor 34 includes a conduit 52 for passing the medium 46" with algae cells 32 downstream. The flow rate of the medium 46" is due solely to gravity and the force of the incoming overflow medium 46' from the chemostat 30. Preferably, the plug flow reactor 34 has a substantially fixed residence time of about one to four days. For purposes of the present invention, the system 10 is provided with a reservoir (not shown) that holds a modified nutrient mix (indicated by arrow 54). Further, the conduit 52 is provided with an input port 50b for receiving the modified nutrient mix 54. In order to manipulate the cellular behavior of algae cells 32 within the plug flow reactor 34, the modified nutrient mix 54 may contain a limited amount of a selected constituent, such as nitrogen or phosphorous. For instance, the nutrient mix 54 may contain no nitrogen. Alternatively, the algae cells 32 may exhaust nutrients such as nitrogen or phosphorous in the nutrient mix 42 at a predetermined point in the plug flow reactor 34. By allowing such nutrients to be exhausted, desired behavior in the algae cells 32 can be caused without adding a specific modified nutrient mix 54. Further, simply water can be added through the modified nutrient mix 54 to compensate for evaporation. In addition to input ports 50a and 50b, the conduit 52 is further provided with an input port 50c to receive other matter.

In the FIGURE, the algae separator 36 is shown in fluid communication with the conduit 52 of the plug flow reactor 34. For purposes of the present invention, the algae separator 36 separates the algae cells 32 from the medium 46" and the remaining nutrients therein through flocculation and/or filtration. As further shown, the algae separator 36 includes an effluence outlet 56 and an algae cell outlet 60. For purposes of the present invention, the system 10 includes a channel 58 providing fluid communication between the effluence outlet 56 and the scrubber 12 through a solution input port 16b in the scrubber chamber 14.

Also, the system 10 includes a cell lysis apparatus 62 that receives algae cells 32 from the algae outlet 60 of the algae separator 36. As shown, the cell lysis apparatus 62 is in fluid communication with an oil separator 64. For purposes of the present invention, the oil separator 64 is provided with two outlets 66, 68. As shown, the outlet 66 is connected to a hydrolysis apparatus 70. Further, the hydrolysis apparatus 70 is connected to the input port 40 in the conduit 38 of the chemostat 30.

Referring back to the oil separator 64, it can be seen that the outlet 68 is connected to a biofuel reactor 72. It is further shown that the biofuel reactor 72 includes two exits 74, 76. For purposes of the present invention, the exit 74 is connected to the input port 50c in the conduit 52 of the plug flow reactor 34. Additionally or alternatively, the exit 74 may be connected to the input port 40 in the chemostat 30. Further, the exit 76 may be connected to a tank or reservoir (not shown) for purposes of the present invention.

In operation of the present invention, pollutant-contaminated flue gas (indicated by arrow 78) is directed from the power plant 18 to the oxidation stage 26. At the oxidation stage 26, nitrogen monoxide in the flue gas 78 is oxidized by nitric acid or by other catalytic or non-catalytic technologies to improve the efficiency of its subsequent removal. Specifically, nitrogen monoxide is oxidized to nitrogen dioxide. Thereafter, the oxidized flue gas (indicated by arrow 80) is delivered from the oxidation stage 26 to the scrubber 12. Specifically, the oxidized flue gas 80 enters the chamber 14 of the scrubber 12 through the input port 16a. Upon the entrance of the flue gas 80 into the chamber 14, the scrubber solution 20 is sprayed within the chamber 14 to absorb, adsorb or otherwise trap the pollutants in the flue gas 80 as is known in the field of scrubbing. With its pollutants removed, the clean flue gas (indicated by arrow 82) exits the scrubber 12 through the gas outlet 24. At the same time, the scrubber solution 20 and the pollutants exit the scrubber 12 through the solution outlet 22.

After exiting the scrubber 12, the scrubber solution 20 and pollutants (indicated by arrow 84) enter the chemostat 30 through the input port 40. Further, the nutrient mix 42 is fed to the chemostat 30 through the input port 40. In the conduit 38 of the chemostat 30, the nutrient mix 42, scrubber solution 20 and pollutants form the medium 46 for growing the algae cells 32. This medium 46 is circulated around the conduit 38 by the paddlewheel 44. Further, the conditions in the conduit 38 are maintained for maximum algal growth. For instance, in order to maintain the desired conditions, the medium 46 and the algae cells 32 are moved around the conduit 38 at a preferred fluid flow velocity of approximately fifty centimeters per second. Further, the amount of algae cells 32 in the conduit 38 is kept substantially constant. Specifically, the nutrient mix 42 and the scrubber solution 20 with pollutants are continuously fed at selected rates into the conduit 38 through the input port 40, and an overflow medium 46' containing algae cells 32 is continuously removed through the output port 48 of the conduit 38.

After entering the input port 50a of the plug flow reactor 34, the medium 46" containing algae cells 32 moves downstream through the conduit 52 in a plug flow regime. Further, as the medium 46" moves downstream, the modified nutrient mix 54 may be added to the conduit 52 through the input port 50b. This modified nutrient mix 54 may contain a limited amount of a selected constituent, such as nitrogen or phosphorous. The absence or small amount of the selected constituent causes the algae cells 32 to focus on energy storage rather than growth. As a result, the algae cells 32 form triglycerides.

At the end of the conduit 52, the algae separator 36 removes the algae cells 32 from the remaining effluence (indicated by arrow 86). Thereafter, the effluence 86 is discharged from the algae separator 36 through the effluence outlet 56. In order to recycle the effluence 86, it is delivered through channel 58 to the input port 16b of the scrubber 12 for reuse as the scrubber solution 20. Further, the removed algae cells (indicated by arrow 88) are delivered to the cell lysis apparatus 62. Specifically, the removed algae cells 88 pass out of the algae cell outlet 60 to the cell lysis apparatus 62. For purposes of the present invention, the cell lysis apparatus 62 lyses the removed algae cells 88 to unbind the oil therein from the remaining cell matter. After the lysing process occurs, the unbound oil and remaining cell matter, collectively identified by arrow 90, are transmitted to the oil separator 64. Thereafter, the oil separator 64 withdraws the oil from the remaining cell matter as is known in the art. After this separation is performed, the oil separator 64 discharges the remaining cell matter (identified by arrow 92) out of the outlet 66 of the oil separator 64 to the input port 40 of the chemostat 30.

In the chemostat 30, the remaining cell matter 92 is utilized as a source of nutrients and energy for the growth of algae cells 32. Because small units of the remaining cell matter 92 are more easily absorbed or otherwise processed by the growing algae cells 32, the remaining cell matter 92 may first be broken down before being fed into the input port 40 of the chemostat 30. To this end, the hydrolysis apparatus 70 is interconnected between the oil separator 64 and the chemostat 30. Accordingly, the hydrolysis apparatus 70 receives the remaining cell matter 92 from the oil separator 64, hydrolyzes the received cell matter 92, and then passes hydrolyzed cell matter (identified by arrow 94) to the chemostat 30.

Referring back to the oil separator 64, it is recalled that the remaining cell matter 92 was discharged through the outlet 66. At the same time, the oil withdrawn by the oil separator 64 is discharged through the outlet 68. Specifically, the oil (identified by arrow 96) is delivered to the biofuel reactor 72. In the biofuel reactor 72, the oil 96 is reacted with alcohol, such as methanol, to create mono-alkyl esters, i.e., biofuel fuel. This biofuel fuel (identified by arrow 98) is released from the exit 76 of the biofuel reactor 72 to a tank, reservoir, or pipeline (not shown) for use as fuel. In addition to the biofuel fuel 98, the reaction between the oil 96 and the alcohol produces glycerin as a byproduct. For purposes of the present invention, the glycerin (identified by arrow 100) is pumped out of the exit 74 of the biofuel reactor 72 to the input port 50c of the plug flow reactor 34.

In the plug flow reactor 34, the glycerin 100 is utilized as a source of carbon by the algae cells 32. Importantly, the glycerin 100 does not provide any nutrients that may be limited to induce oil production by the algae cells 32 or to trigger flocculation. The glycerin 100 may be added to the plug flow reactor 34 at night to aid in night-time oil production. Further, because glycerin 100 would otherwise provide bacteria and/or other non-photosynthetic organisms with an energy source, limiting the addition of glycerin 100 to the plug flow reactor 34 only at night allows the algae cells 32 to utilize the glycerin 100 without facilitating the growth of foreign organisms. As shown in the FIGURE, the exit 74 of the biofuel reactor 72 may also be in fluid communication with the input port 40 of the chemostat 30 (connection shown in phantom). This arrangement allows the glycerin 100 to be provided to the chemostat 30 as a carbon source.

While the particular Photosynthetic Carbon Dioxide Sequestration and Pollution Abatement as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for producing biofuel from pollutant-fed algae which comprises:
   a scrubber having a chamber for receiving a pollutant-contaminated flue gas stream and an outlet for releasing cleaned flue gas;
   a liquid scrubber solution received in the chamber for scrubbing the pollutant-contaminated gas stream, wherein the scrubber solution is a sodium-based liquid solution for absorbing carbon-rich pollutants from the pollutant-contaminated gas stream to produce a carbon-rich liquid scrubber solution;
   a bioreactor for growing algae cells with high oil content, said bioreactor having an input port for receiving the carbon-rich liquid scrubber solution with absorbed carbon-rich pollutants for use of the absorbed carbon-rich pollutants as nutrients in a medium to support algae cell growth;
   an algae separator in fluid communication with the bioreactor for removing the algae cells from the medium to create an effluence;
   a channel for recycling the effluence from the algae separator to the scrubber for use as the liquid scrubber solution;
   an oil separator in fluid communication with the algae separator for withdrawing oil in the algae from the remaining cell matter;
   a channel for recycling the remaining cell matter from the oil separator to a hydrolysis device to produce hydrolyzed cell matter for return to a chemostat of the bioreactor to further support algae cell growth; and
   a reactor for receiving the oil from the oil separator and to synthesize biofuel and byproduct from said oil.

2. A system as recited in claim 1 wherein the pollutants are selected from a group comprising carbon dioxide, sulfur oxides and nitrogen oxides.

3. A system as recited in claim 1 wherein the liquid scrubber solution is selected from a group comprising sodium hydroxide and sodium bicarbonate.

4. A system as recited in claim 1 further comprising an oxidation unit for treating the pollutant-contaminated gas stream before being received in the scrubber.

5. A system as recited in claim 4 wherein the oxidation unit oxidizes nitrogen monoxide in the pollutant-contaminated gas stream.

6. A system as recited in claim 1 wherein the bioreactor comprises:
   at least one chemostat formed with a conduit for growing algae therein, wherein the chemostat includes the input port for receiving the liquid scrubber solution and for receiving a nutrient mix to form a medium for maximum algae growth, and wherein the chemostat has an output port for passing the medium with algae growth from the conduit of the chemostat;
   a means for continuously moving the medium through the conduit of the chemostat at a predetermined fluid flow velocity;
   a plug flow reactor formed with a conduit having an input port for receiving the medium with algae growth from the chemostat; and
   a means for adding a modified nutrient mix to the medium with algae growth in the plug flow reactor, wherein the modified nutrient mix comprises a limited amount of a selected constituent to trigger high oil production in the algae growth.

7. A system as recited in claim 6 further comprising:
   an apparatus for lysing the algae cells removed from the conduit to unbind oil within the algae cells for transfer of the oil from the oil separator to the reactor for synthesizing biofuel and glycerin from said oil; and
   a means for recycling at least one byproduct to the bioreactor to support growth of algae cells with high oil content.

8. A system as recited in claim 7 wherein the remaining cell matter is a byproduct and the glycerin is a byproduct.

9. A system for producing biofuel from pollutant-fed algae which comprises:
   a means for scrubbing a pollutant-contaminated flue gas stream with a liquid scrubber solution, wherein the liquid scrubber solution is a sodium-based liquid solution for absorbing carbon-rich pollutants from the pollutant-contaminated flue gas stream to produce a carbon-rich liquid scrubber solution, wherein said means for scrubbing comprises an outlet for releasing cleaned flue gas;
   a means for feeding the carbon-rich liquid scrubber solution to a bioreactor to form a medium therein to support algae cell growth;
   a means for promoting growth of high oil content algae cells in the medium in the bioreactor, with said algae cells converting the absorbed carbon-rich pollutants from the carbon-rich liquid scrubber solution into cell matter during cell growth;
   a means for separating the algae cells from the medium in the bioreactor to form an effluence;
   a means for recycling the effluence for use as the liquid scrubber solution;
   a means for withdrawing oil in the algae cells from the remaining cell matter;
   a means for receiving the oil from the means for withdrawing the oil to synthesize biofuel and glycerin from said oil; and
   a means for recycling the remaining cell matter from the withdrawing means, for hydrolysis and return as hydrolyzed cell matter to the cell growth promoting means to further support algae cell growth.

10. A system as recited in claim 9 further comprising a means for oxidizing the pollutant-contaminated gas stream.

11. A system as recited in claim 9 wherein the pollutants are selected from a group comprising carbon dioxide, sulfur oxides, and nitrogen oxides.

12. A system as recited in claim 9 wherein the liquid scrubber solution is selected from a group comprising sodium hydroxide and sodium bicarbonate.

13. A method for producing biofuel from pollutant-fed algae which comprises the steps of:
   scrubbing a pollutant-contaminated flue gas stream with a liquid scrubber solution in a scrubber, wherein the liquid scrubber solution is a sodium-based liquid solution for absorbing carbon-rich pollutants from the pollutant-contaminated flue gas stream to produce a carbon-rich liquid scrubber solution, wherein said scrubber comprises an outlet for releasing cleaned flue gas;

feeding the carbon-rich liquid scrubber solution to a bioreactor wherein the bioreactor includes at least one chemostat and a plug flow reactor, and wherein the chemostat is formed with a conduit for growing algae therein and an input port for receiving the carbon-rich liquid scrubber solution and a nutrient mix to form a medium for maximum algae growth, with the chemostat having an output port for passing the medium with algae growth from the conduit of the chemostat, and further wherein the plug flow reactor is formed with a conduit having an input port for receiving the medium with algae growth from the chemostat;

growing algae cells with high oil content in the bioreactor, with said algae cells converting the carbon-rich pollutants from the carbon-rich liquid scrubber solution into cell matter during cell growth;

separating the algae cells from an effluence from the bioreactor to create the effluence;

recycling the effluence for use as the liquid scrubber solution;

processing oil from the algae cells to form biofuel; withdrawing oil in the algae cells from the remaining cell matter;

synthesizing biofuel and byproduct from the oil with a reactor;

hydrolyzing the remaining cell matter from the withdrawing step to create hydrolyzed cell matter; and recycling the hydrolyzed remaining cell matter to the bioreactor to further support algae cell growth.

14. A method as recited in claim 13 further comprising the step of treating the pollutant-contaminated gas stream before the scrubbing step.

15. A method as recited in claim 14 wherein the treating step includes oxidizing nitrogen oxides in the pollutant-contaminated gas stream.

16. A method as recited in claim 13 wherein the pollutants are selected from a group comprising carbon dioxide, sulfur oxides, and nitrogen oxides.

17. A method as recited in claim 13 wherein the liquid scrubber solution is selected from a group comprising caustic soda and sodium bicarbonate.

18. A method as recited in claim 13 wherein the bioreactor includes at least one chemostat and a plug flow reactor, and wherein the chemostat is formed with a conduit for growing algae therein and an input port for receiving the carbon-rich liquid scrubber solution and a nutrient mix to form a medium for maximum algae growth, with the chemostat having an output port for passing the medium with algae growth from the conduit of the chemostat, and further wherein the plug flow reactor is formed with a conduit having an input port for receiving the medium with algae growth from the chemostat, with the method further comprising the steps of:

continuously moving the medium through the conduit of the chemostat at a predetermined fluid flow velocity; and adding a modified nutrient mix to the medium with algae growth in the plug flow reactor, wherein the modified nutrient mix comprises a limited amount of a selected constituent to trigger high oil production in the algae growth.

19. A method as recited in claim 18 wherein the processing step includes:

lysing the algae cells removed from the conduit to unbind oil within the algae cells; and withdrawing the oil from remaining cell matter.

20. A method as recited in claim 19 wherein the remaining cell matter is a byproduct and glycerin is a byproduct, and wherein the processing step includes recycling at least one byproduct to the bioreactor to support growth of algae cells with high oil content.

* * * * *

UNITED STATES PATENT AND TRADEMARK OFFICE
CERTIFICATE OF CORRECTION

PATENT NO. : 8,262,776 B2
APPLICATION NO. : 11/549541
DATED : September 11, 2012
INVENTOR(S) : David A. Hazlebeck and Eric H. Dunlop Page 1 of 1

It is certified that error appears in the above-identified patent and that said Letters Patent is hereby corrected as shown below:

In the Specification

Col. 1, Line 3-5 should read

The U.S. Government has a paid-up license in this invention and the right in limited circumstances to require the patent owner to license others on reasonable terms as provided for by the terms of Contract No. HR0011-09-C-0034 awarded by DARPA.

Signed and Sealed this
Eighteenth Day of June, 2013

Teresa Stanek Rea
*Acting Director of the United States Patent and Trademark Office*